United States Patent
Koenig et al.

(10) Patent No.: US 9,581,572 B2
(45) Date of Patent: Feb. 28, 2017

(54) DEVICE FOR DETERMINING PROPERTIES OF A MEDIUM

(71) Applicants: BUERKERT WERKE GMBH, Ingelfingen (DE); BUERKERT SAS, Triembach au Val (FR)

(72) Inventors: Bertrand Koenig, Saint Pierre Bois (FR); Yves Hoog, Maisongoutte (FR); Christophe Gittinger, Westhouse (FR); Yannick Fuchs, Logelbach (FR)

(73) Assignee: BUERKERT WERKE GMBH (DE)

( * ) Notice: Subject to any disclaimer, the term of this patent is extended or adjusted under 35 U.S.C. 154(b) by 246 days.

(21) Appl. No.: 14/297,399

(22) Filed: Jun. 5, 2014

(65) Prior Publication Data
US 2014/0360270 A1 Dec. 11, 2014

(30) Foreign Application Priority Data
Jun. 5, 2013 (FR) ...................................... 13 55162

(51) Int. Cl.
*G01N 29/02* (2006.01)
*G01N 29/22* (2006.01)
(Continued)

(52) U.S. Cl.
CPC ......... *G01N 29/221* (2013.01); *G01N 29/022* (2013.01); *G01N 29/024* (2013.01);
(Continued)

(58) Field of Classification Search
CPC ........................... G01N 29/022; G01N 29/024
(Continued)

(56) References Cited

U.S. PATENT DOCUMENTS

| 4,691,714 A | 9/1987 | Wong et al. .................. 128/738 |
| 2012/0060591 A1 | 3/2012 | Faustmann et al. ......... 73/64.53 |
| 2014/0083194 A1* | 3/2014 | Faustmann .......... G01N 29/022 |
| | | 73/629 |

FOREIGN PATENT DOCUMENTS

| WO | WO 2008/034878 | 3/2008 | ............. G01N 29/02 |
| WO | WO 2010/118793 | 10/2010 | ........... G01N 29/032 |

(Continued)

OTHER PUBLICATIONS

French Search Report issued in corresponding French Patent Appln. No. FR1355162 dated May 23, 2014 (7 pgs).

*Primary Examiner* — John Chapman, Jr.
(74) *Attorney, Agent, or Firm* — Hayes Soloway P.C.

(57) ABSTRACT

A device for determining properties of a medium has a hollow body which accommodates the medium and a housing which circumferentially surrounds the hollow body. At least one portion of a wall of the hollow body is formed as waveguide for acoustic surface waves, which forms an interface to the medium. There is provided at least one transmitter for exciting acoustic waves in the waveguide and at least one receiver for receiving acoustic waves from the waveguide, which are arranged at a distance from each other, wherein the transmitter and the receiver are in direct contact with an outer surface of the waveguide and wherein the distance between transmitter and receiver is chosen such that acoustic waves excited by the transmitter can at least partly propagate on paths extending through the medium. There is provided at least one contact carrier on which the transmitter and/or the receiver are arranged. Between the waveguide and the contact carrier a continuous air gap is formed. The space between the hollow body, the contact carrier and the housing is filled with a filling mass.

17 Claims, 4 Drawing Sheets

(51) Int. Cl.
*G01N 29/024* (2006.01)
*G01N 29/24* (2006.01)

(52) U.S. Cl.
CPC ... *G01N 29/2462* (2013.01); *G01N 2291/044* (2013.01); *G01N 2291/0423* (2013.01); *G01N 2291/0426* (2013.01); *G01N 2291/0428* (2013.01); *G01N 2291/102* (2013.01); *G01N 2291/2634* (2013.01)

(58) Field of Classification Search
USPC ....................................................... 73/64.53
See application file for complete search history.

(56) References Cited

FOREIGN PATENT DOCUMENTS

| WO | WO 2010/136350 | 12/2010 | ............. G01N 29/22 |
| WO | WO 2012/156517 | 11/2012 | ............. G01N 29/02 |

\* cited by examiner

DEVICE FOR DETERMINING PROPERTIES OF A MEDIUM

FIELD OF THE INVENTION

The invention relates to a device for determining properties of a medium.

BACKGROUND

The measurement of certain properties of a medium can be effected by using acoustic waves. For this measurement method, which is described for example in WO 2008/034878 A2 or WO 2010/136350 A1, the medium is in direct contact with an acoustic waveguide. In the waveguide acoustic surface waves are excited, wherein the type and frequency of the surface waves are chosen such that a partial coupling out into the medium is effected. A part of the acoustic surface waves in the waveguide therefore is coupled into the medium as longitudinal volumetric sound waves. These sound waves pass through the medium and are reflected on a surface bordering the medium such that they again impinge on the waveguide. There, a part of the volumetric sound waves again is coupled into the waveguide as acoustic surface waves and runs on in the same. At an acoustic receiver, which is arranged at the waveguide spaced from the transmitter, a characteristic signal thereby is obtained, whose temporal course of intensity including the time delay with respect to the signal sent by the transmitter permits conclusions regarding characteristic properties of the medium such as sound velocity, temperature, homogeneity, flow velocity, flow rate, concentration or viscosity.

This measurement method is suitable in particular for liquid, but also for highly viscous, dough-like, gel-like or pasty media of homogeneous or inhomogeneous nature, including biological samples. The use for gaseous media would also be conceivable. When the medium flows through the device, temporal changes of the medium can also be detected.

The spatial propagation of the volumetric sound waves in the medium for example is achieved in that the volumetric sound waves are coupled out into the medium at an angle $\delta$ based on a surface normal of the waveguide. The relation can be described by the following formula:

$$\delta = \arcsin\left(\frac{c_M}{c_S}\right),$$

wherein $c_M$ is the sound velocity of the volumetric sound waves inside the medium and $c_S$ is the sound velocity of the acoustic surface waves propagating along the waveguide.

In the most frequent case, in which the sound velocity in the medium is smaller than that of the surface waves in the waveguide, sound waves are coupled out at an angle different from 0, and the volumetric sound waves cover a spatial distance along the waveguide, possibly by multiple reflection within the medium.

In the known devices, transmitter and receiver are mounted on a side of the waveguide opposite the interface with the medium. To ensure that surface sound waves excited on this side of the waveguide can be coupled into the medium, Lamb waves therefore preferably are excited, i.e. waves whose wavelength is much longer than the thickness of the waveguide between transmitter and medium. In this case, both the upper and the lower side of the waveguide are moving, wherein the vibration also has a longitudinal component. Therefore, this type of excitation is suitable for coupling out volumetric sound waves. It is also possible to chose the wavelength of the excited acoustic surface waves in the order of magnitude of the thickness of the waveguide, wherein then surface waves are excited in a transition region between Lamb waves and Rayleigh waves.

The devices described so far in the prior art, which operate by the principle described above, have a complex construction and are expensive to manufacture.

Therefore, it is the object of the invention to create a simply constructed and easily manufacturable device for determining properties of a medium by means of the excitation of surface sound waves.

SUMMARY

The invention provides a device for determining properties of a medium with a preferably cylindrical hollow body which accommodates the medium, wherein at least one portion of a wall of the hollow body is formed as waveguide for acoustic surface sound waves, which forms an interface to the medium. There is provided at least one transmitter for exciting acoustic waves in the waveguide and at least one receiver for receiving acoustic waves from the waveguide, which are arranged spaced from each other, wherein the transmitter and the receiver are in direct contact with an outer surface of the waveguide. The distance between transmitter and receiver is chosen such that acoustic waves excited by the transmitter can at least partly propagate on paths extending through the medium. There is provided at least one contact carrier on which the transmitter and/or the receiver is arranged, wherein between the waveguide and the contact carrier a continuous air gap is formed. The device has a housing which circumferentially surrounds the hollow body. The space between the hollow body, the contact carrier and the housing is filled with a filling mass.

The air gap preferably is completely closed and sealed towards the outside.

The contact carrier, e.g. with already pre-mounted transmitter and receiver, is easily mountable on the outside of the in particular tubular waveguide. The distance between transmitter and receiver can be specified precisely by the contact carrier. The housing only must be placed around the hollow body and be filled with the filling mass. In general, the device can be constructed of few individual parts and be manufactured without great expenditure, wherein nevertheless a high precision e.g. in the positioning of transmitter and receiver can be achieved.

Instead of a single contact carrier, a plurality of contact carriers can also be provided, which together cover the air gap.

Although transmitter and receiver can be arranged in the region of a single air gap, only one transmitter and only one receiver alternatively might be provided in the region of an air gap, while the counterpart (transmitter or receiver) is located at another point of the hollow body, e.g. under a further air gap covered by a contact carrier.

The filling mass may consist of a material which absorbs acoustic waves excited by the transmitter, e.g. the acoustic surface waves. In the hollow body, substantially all acoustic surface waves can be absorbed, which do not extend in the region directly radially inwards of the air gap, i.e. on the inside, and thus a propagation of acoustic surface waves remote from the region directly below the air gap is prevented. Due to the presence of the filling mass, a coupling out of acoustic surface sound waves from the volumetric sound waves impinging on the hollow body from the medium optionally can be suppressed, so that such coupling out substantially only is effected in the region of the hollow body which is located directly below the air gap. In this case, the waveguide would be defined exclusively by the portion of the wall of the hollow body between transmitter and receiver directly below the air gap.

The thickness of the filling mass can be chosen distinctly larger than the thickness of the waveguide, so that surface waves can be absorbed well outside the region of the waveguide which is not located directly radially inwards of the air gap.

Thus, the air gap on the one hand can serve to prevent the measurement from being distorted by the contact carrier resting on the waveguide, but on the other hand also to unambiguously define the waveguide substantially on the inside of the contact carrier between transmitter and receiver.

In the second case it is favorable when the cylindrical hollow body is completely covered by the filling mass outside the air gap, at least over the axial length of the contact carrier. The filling mass, however, may be provided axially beyond the contact carrier, so that it also protects the same against environmental influences.

The space between the hollow body, the contact carrier and the housing is completely filled with the filling mass, e.g. with the exception of the air gap.

A suitable filling mass for example is an epoxy resin or polyurethane, but there might also be used e.g. an oil or sand. Filling the space between hollow body and housing can be effected in any suitable way, e.g. by potting.

The contact carrier can be arranged in longitudinal direction of the cavity, so that transmitter and receiver are spaced from each other in the longitudinal direction. When the hollow body is a circularly cylindrical tube, the contact carrier need not follow the curvature of the tube, but is located along a straight line. When the medium flows through the hollow body or past the waveguide, the straight line is located between transmitter and receiver e.g. parallel to the flow direction.

The contact carrier and the air gap can be formed strip-shaped, i.e. have a greater longitudinal extension than their width. The longitudinal extension between transmitter and receiver, which also corresponds to a minimum length of the waveguide, is chosen so long that the volumetric sound waves which propagate in the medium interact with the inner surface of the waveguide at several points spaced from each other, wherein at each of these points a coupling out of acoustic surface waves can be effected.

The contact carrier itself can be formed by a printed circuit board, as in this way the necessary electrical contacting of the transmitter and receiver can be achieved easily and at low cost.

To provide for further measurement methods or also to improve the accuracy of the measurement results, it is possible to arrange several assemblies of contact carrier, transmitter and receiver distributed over the circumference of the hollow body. These assemblies are e.g. located axially at the same height, wherein the transmitters and the receivers each are arranged axially at the same height.

It would theoretically be conceivable to arrange at least one further receiver on the contact carrier between transmitter and receiver, so that e.g. runtime differences of the signal can be detected more easily. It would also be possible to place a transmitter in the middle of the contact carrier and provide receivers at both ends of the contact carrier, which would facilitate a measurement of a flow velocity of the medium.

In any case it can be advantageous when transmitter and receiver are formed such that their function can be exchanged, i.e. the transmitter can also be operated as receiver and/or the receiver can also be operated as transmitter.

Transmitter and receiver are designed such that individual wave pulses offset in time can be excited and the same can also be temporally resolved upon receipt. What can be measured at least is the intensity, frequency and/or runtime delay of the signals.

Transmitter and/or receiver preferably operate piezoelectrically, they may include piezoelectric interdigital transducers. Transmitter and/or receiver each can be formed by a piezoelectric transducer with interdigital electrodes.

The waveguide and the entire hollow body on the other hand advantageously are made of a non-piezoelectric material. In addition, the waveguide can be homogeneously formed of a single material over its entire extension. As material of the waveguide, a metal is used, e.g. a stainless steel or a plastic material, as polyether ether ketone (PEEK) or polyoxymethylene (POM).

The hollow body can be is a single-walled tube which in particular is circularly cylindrical in cross-section and in which the medium is accommodated.

The tube can be a portion of a line, so that the media flowing in the line are measured during their passage.

The waveguide e.g. is an integral part of the hollow body and formed by a wall portion of the hollow body, but it can differ from the rest of the hollow body e.g. by the geometry of its outer and/or inner surface. Thus, it is possible to partly vary the shape of the surface and also the thickness of the hollow body and optionally also of the waveguide, in order to selectively cause differences in the propagation of the surface waves.

The thickness of the waveguide is defined here as distance between the inner and the outer surface of the hollow body in particular in the region of the air gap, as measured vertically to a surface normal of the hollow body in this region. The thickness (and hence the wall thickness of the hollow body) should be chosen such that the excited surface waves propagate along both surfaces of the waveguide.

The wall thickness of the hollow body can be the same over the entire region in which the same acts as waveguide. This also is possible when several transmitters and/or receivers are mounted on the outer surface of the waveguide, as then all acoustic surface waves can propagate on the waveguide under identical conditions.

On the inside of the contact carrier, the surface of the hollow body which forms the waveguide can be formed flat, so that the boundary of the air gap is formed by a flattened portion. This design facilitates sealing of the air gap. By removing the surface of the hollow body, in particular in the case of a circularly cylindrical tube, the propagation behavior, excitation behavior, frequency and wavelength of the excited surface waves also can be influenced.

The air gap advantageously is formed completely between the waveguide, the contact carrier and the transmitter and receiver, and no further components are required.

To facilitate mounting of the contact carrier on the hollow body and sealing of the air gap, the contact carrier can include a longitudinally extending depression, wherein the air gap can be limited to the region of the depression. The depression is formed e.g. by a longitudinal groove in the contact carrier, which faces the hollow body and which defines the air gap together with the hollow body. Such longitudinal groove can be fabricated easily and at low cost for example by milling out e.g. a printed circuit board.

The edges of the contact carrier defining the longitudinal groove can be adhered to the hollow body.

Transmitter and receiver each may be attached to one end of the contact carrier, and in one possible embodiment they terminate the long-side ends of the longitudinal groove and thus of the air gap.

When several contact carriers are used, which each are connected only with a transmitter or receiver, the longitudinal groove need not extend along the entire length of the contact carrier.

Transmitter and receiver are bonded to the contact carrier e.g. with an electrically conductive adhesive, which facilitates contacting.

The assembly of contact carrier, transmitter and receiver can easily be prefabricated and as a whole be attached to the waveguide.

During the attachment, transmitter and receiver can be bonded to the waveguide, i.e. to the hollow body, e.g. with an acoustically conductive adhesive, as here a good acoustic coupling between the transmitter or receiver and the hollow body is important.

Alternatively, transmitter and receiver also can first be bonded to the hollow body and subsequently the contact carrier can be mounted, e.g. likewise by bonding.

The contact carrier is bonded to the hollow body, i.e. to the waveguide, e.g. likewise with an electrically conductive adhesive, so that the entire assembly of contact carrier, transmitter and receiver can be grounded via the hollow body. The adhesive can be applied along the entire lateral longitudinal edges of the longitudinal groove. This bonding also can serve to laterally seal the air gap.

A plug attached to the contact carrier simplifies the electrical contacting of the transmitter and the receiver for energy supply and data transmission. The attachment of the plug to the contact carrier may be effected by soldering.

By a control and evaluation unit data can be transmitted to the transmitter and from the receiver. The control and evaluation unit can be integrated into the device or be arranged separate from the same.

The control and evaluation unit can easily be accommodated in the housing, wherein a cable connected to the plug can lead to the control and evaluation unit. The cable can be fixed by the filling mass, wherein it is also potted e.g. when filling the space between hollow body and housing. In this way, the connection between cable and plug as well as the plug itself are protected well even against excessive forces.

The evaluation of the signals of the receiver can be effected completely in the control and evaluation unit of the device.

The data of the control and evaluation unit can be displayed on a display arranged at the housing. It is also possible to connect a further electronic unit with a cable or to provide a radio module which wirelessly transmits the data to another electronic unit.

The hollow body can be part of a fluid system. The hollow body may include end-side fastening portions for the fluid connection with a fluid system. The end-side fastening portions can be provided in the form of flanges, which allows to easily integrate the device into an existing fluid system.

Apart from the fluid connections no further openings must be provided in the hollow body, so that the device nowhere must be sealed against the medium. Thus, aggressive or sensitive media also can be measured in the device in a simple way.

The housing can be arranged concentrically around the hollow body. It has no contact with the medium.

It is possible to fix the housing at the hollow body only by the filling mass and to use no additional fastening means. In addition to the filling mass, the housing might however also be connected with the hollow body by bonding, soldering, welding or other suitable fastening measures.

The housing may have a tubular portion which is pushed over the hollow body. Alternatively, the multipart housing might e.g. also consist of two shells, for example, which are put together around the hollow body.

When the hollow body includes fastening means for arrangement in a fluid system, e.g. flanges, the same advantageously are mounted on the hollow body after mounting the housing around the hollow body or after filling the interspace. This can be accomplished for example by welding flange pieces or by shaping the ends of the hollow body.

The measurement principle of the device according to the invention is based on the fact that the transmitter excites acoustic surface waves in the waveguide, which on the one hand extend along the waveguide and on the other hand couple out a part of their energy on the surface of the waveguide opposite the transmitter into the medium as volumetric sound waves. These volumetric sound waves pass through the medium, are reflected on an opposed wall of the hollow body and thus get back to the waveguide. There, a part of the energy of the volumetric sound waves is again converted and coupled in back into the waveguide as acoustic surface sound wave. This operation can be effected at several points of the waveguide, as due to the relation between the angle of coupling out and the ratio of the sound velocities the propagation of the volumetric sound waves is effected with a component directed along the waveguide.

When the thickness of the waveguide is distinctly smaller than the wavelengths of the acoustic surface waves, the amplitude of the excited Lamb waves substantially is identical on both surfaces of the waveguide. On the other hand, when the thickness of the waveguide lies in the same order of magnitude as the wavelength of the acoustic surface waves, the amplitude of the surface waves generally differs between the surface on which the surface wave is excited and the opposite surface. In both cases, however, it is possible to couple out longitudinal volumetric sound waves, as on both surfaces the surface sound waves also each have a longitudinal component.

The receiver either exclusively receives the surface sound waves arriving at the same along the waveguide or also volumetric sound waves which are passed on to the same through the region of the waveguide located directly below the receiver. With reference to the temporal course of the received signal intensity, conclusions as to the properties of the medium inside the hollow body can be drawn as known.

When the excitation of the surface sound waves by the transmitter is effected in individual wave pulses, it is favorable to choose the time interval between two wave pulses such that both the direct surface waves and all detectable volumetric sound waves already have arrived at the receiver, before the next pulse is triggered. The runtime difference between the surface waves and the volumetric sound waves as well as the course of intensity of a pulse for the various propagation paths allow to draw conclusions as to the properties of the medium.

DETAILED DESCRIPTION

Figure 1:
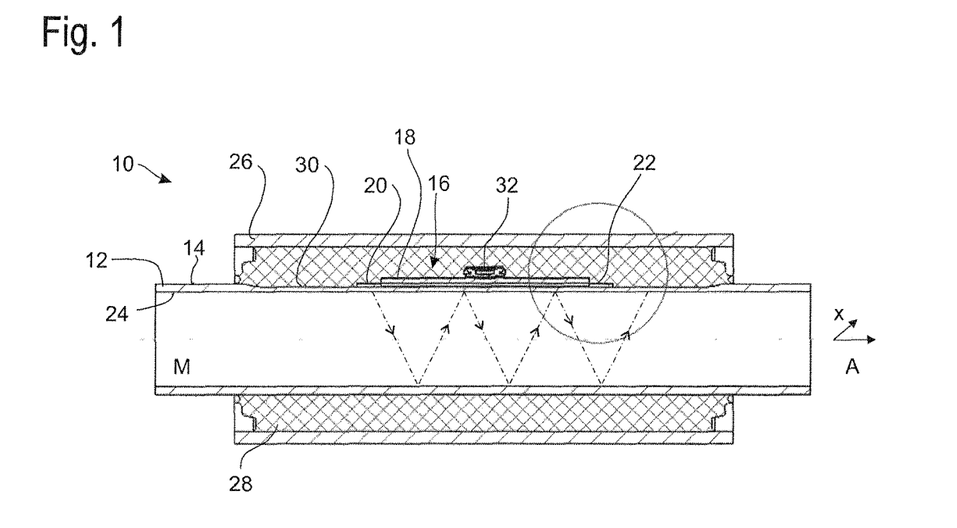
FIG. 1 shows a schematic longitudinal section of a device according to the invention.

FIG. 1 shows a sectional view of a device 10 for determining properties of a medium M which is present in a tubular hollow body 12 and for example flows through the same.

On a radially outer surface 14 of the hollow body 12, an assembly 16 comprising a contact carrier 18, a piezoelectric transmitter 20 and a piezoelectric receiver 22 is arranged.

Transmitter 20 and receiver 22 here are designed such that they can also be operated in the respective other function, i.e. the transmitter 20 as receiver and the receiver 22 as transmitter.

The radially inner surface 24 of the hollow body 12 forms an interface to the medium M.

In this case, the hollow body 12 is a stainless steel tube which, in particular when it is connected with a fluid system likewise consisting of metal tubes, in a simple way also serves as grounding for the electronic components.

A housing 26 concentrically surrounds the hollow body 12. The space between the outer surface 14 of the hollow body 12 and the inner surface of the housing 26 is filled with a filling mass 28 which in this example cures to form a rigid solid body. The filling mass 28 for example can be polyurethane or an epoxy resin.

In the region of the contact carrier 18 the outer surface 14 of the hollow body 12 is flattened, for example by milling off a part of the outer circumference. This flattened portion 30 extends in longitudinal direction A beyond the contact carrier 18, while in its transverse direction x it substantially corresponds to the width of the contact carrier 18 (see FIGS. 1 and 3).

Figure 7:
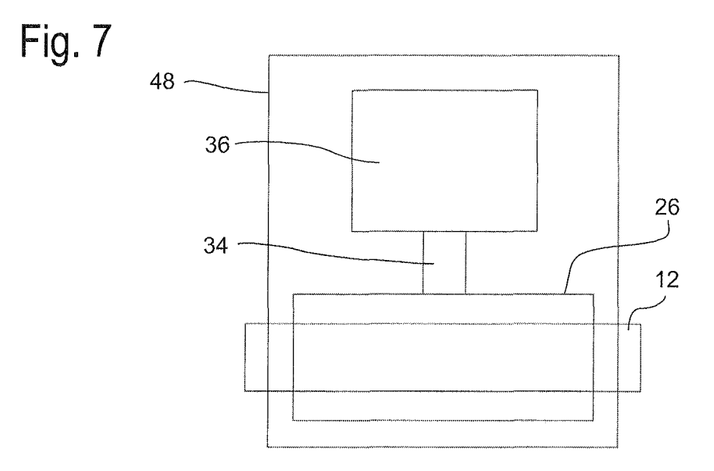
FIGS. 7 and 8 show possible arrangements of a control unit in a device according to the invention.
Figure 8:
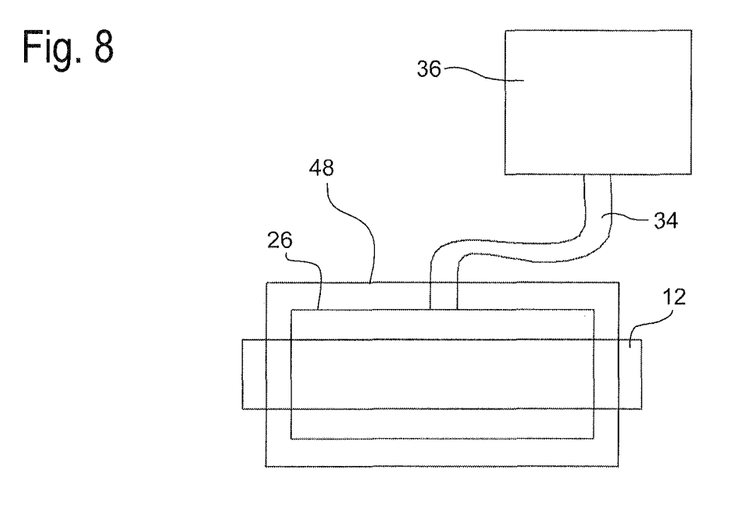

The electrical contacting and the excitation of vibration signals in the transmitter 20 or the reading out of the receiver 22 is effected via a plug 32 arranged at the contact carrier 18, on which a cable 34 is mounted, which leads to a control and evaluation unit 36 (see FIGS. 7 and 8).

In this exemplary embodiment the contact carrier 18 is formed by a printed circuit board, wherein all electric lines for the energy supply, for control and for reading out the measurement data are designed as conductor paths in the printed circuit board or on the printed circuit board.

The plug 32 directly contacts conductor paths on the printed circuit board. Thus, the contact carrier 18 here is made of a non-piezoelectric material.

Transmitter 20 and receiver 22 are piezoelectric transducers which for example are provided with interdigital electrodes, wherein the electrodes are in direct contact with the outer surface 14 of the hollow body 12.

Figure 2:
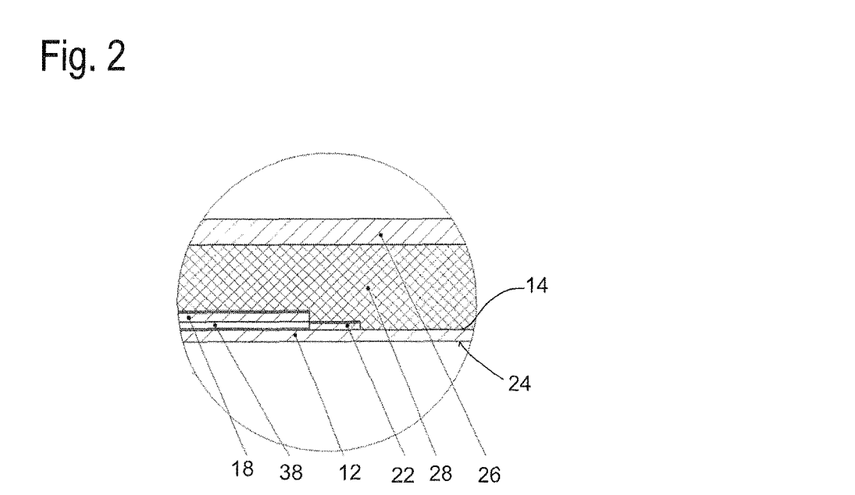
FIG. 2 shows a magnification of the encircled portion of the device of FIG. 1.

FIG. 2 shows a detail view of the region of the device 10 marked by the circle.

It can be seen here that the contact carrier 18 partly is arranged at a distance from the outer surface 14 of the hollow body 12. Between the bottom side of the contact carrier 18 and the outer surface 14 of the hollow body 12 an air gap 38 is formed. The filling mass 28 leaves this air gap 38 open, but otherwise completely surrounds the contact carrier 18 as well as the transmitter 20 and the receiver 22. The filling mass 28 circumferentially surrounds the hollow body 12 with the exception of the air gap 38 and also extends in longitudinal direction A beyond the assembly 16 of contact carrier 18, transmitter 20 and receiver 22.

Figure 3:
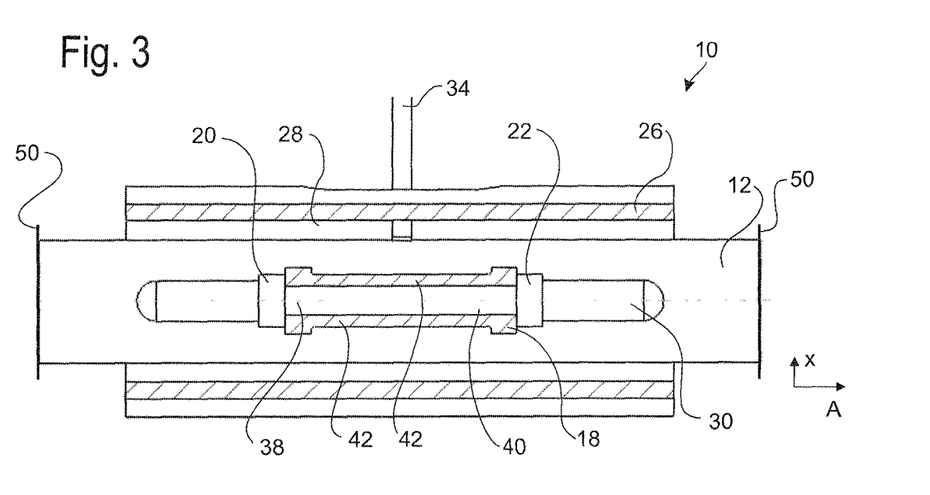
FIG. 3 shows a schematic longitudinal section of the device of FIG. 1 at the level of the contact carrier.

FIG. 3 shows a longitudinal section through the device 10 at the level of the air gap 38. It can be seen that the transmitter 20 and the receiver 22 each directly rest on the outer surface 14 of the hollow body 12 in the flattened portion 30. The contact carrier 18, on the other hand, has a longitudinal groove 40 which extends along the complete length of the contact carrier 18 between transmitter 20 and receiver 22. The two longitudinal edges 42 of the contact carrier 18, which define the longitudinal groove 40, continuously extend from the transmitter 20 to the receiver 22. Along their entire length, they continuously are firmly connected with the hollow body 12 in the region of the flattened portion 30 with an electrically conductive, heat-resistant adhesive (see FIG. 6).

Transmitter 20 and receiver 22 can extend beyond the flattened portion 30 in the longitudinal direction A.

At both axial ends, the hollow body 12 here includes end-side fastening portions 50 for the fluid connection with a non-illustrated fluid system.

Figure 4:
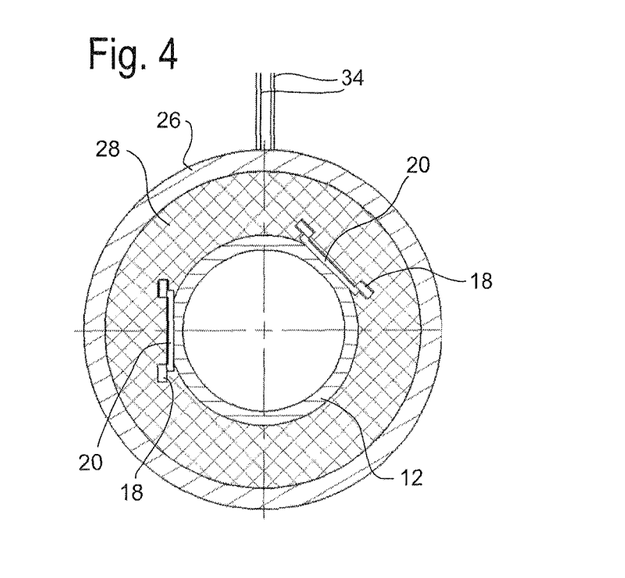
FIG. 4 shows a schematic cross-section of the device of FIG. 1 in the region of the transmitter and/or receiver.
Figure 5:
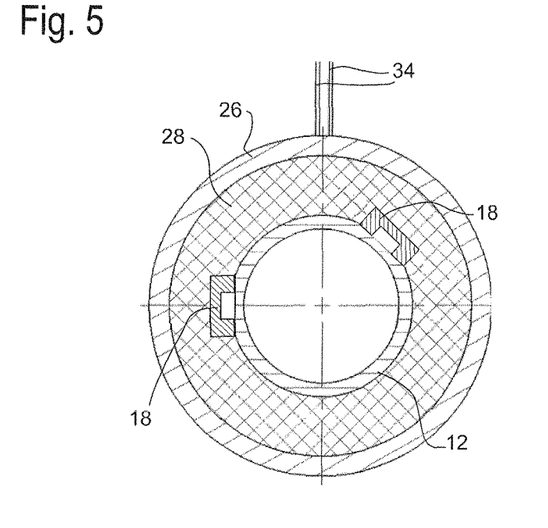
FIG. 5 shows a schematic cross-section of the device of FIG. 1 in the region of the air gap.

FIGS. 4 and 5 show cross-sections through the device 10, on the one hand in the region of the transmitter 20 (and of the receiver 22) and in the region of the air gap 38. In the example shown there, two flattened portions 30 each are formed on the circumference of the hollow body 12, which here are not directly diametrically opposed, although this can also be advantageous. On each of the flattened portions 30 an assembly 16 is arranged. The respective assemblies 16 of contact carrier 18, transmitter 20 and receiver 22 are identical in construction and each are fixed at the hollow body 12 at the same axial position.

Of course, only one single assembly 16 or more than two assemblies 16 also might be provided at the hollow body 12.

The surface waves emitted by the transmitter 20 of the one assembly 16, at least those which traverse the medium M as volumetric sound wave, also are detectable by the receiver 22 of one of the other assemblies 16.

For carrying out a measurement of properties of the medium M in the interior of the hollow body 12, the transmitter 20 excites acoustic surface waves in the region of the hollow body 12 directly below the electrodes of the transmitter 20. These surface waves extend along the hollow body 12, which in this region represents a waveguide, among other things in direction to the receiver 22 and are detected there. Due to the direct interface of the medium M to the waveguide, a part of the energy of the acoustic surface waves is coupled out on the inner surface 24 of the hollow body 12 at the interface to the medium M and from there passes through the medium M as volumetric sound wave at a specific propagation angle (see FIG. 1). On the opposite wall of the hollow body 12, this volumetric sound wave again impinges on the hollow body 12 and is reflected. In this way, the volumetric sound wave propagates through the medium. Whenever the volumetric sound wave impinges on the wall of the hollow body 12, it is possible that acoustic surface waves in turn are coupled into the hollow body 12. Said waves then pass through the wall of the hollow body 12 serving as waveguide to the receiver 22 and are likewise detected there. From the runtime delay between a wave pulse emitted by the transmitter 20 and the signal arriving at the receiver 22 as well as its intensity and time course, conclusions can be drawn as to the properties of the medium M, such as its concentration, viscosity, sound velocity, flow velocity, flow rate, temperature and homogeneity.

The entire hollow body 12 can act as waveguide, but here substantially only the region of the hollow body 12 in the flattened portion 30 below the air gap 38 between transmitter 20 and receiver 22 each is active as waveguide. The delimitation can be influenced by the presence of the filling mass 28 in contact with the remaining surface of the hollow body 12 and/or the geometrical change in thickness as formed by the flattened portion 30 or the surface structure of the hollow body 12.

Before attachment to the hollow body 12, contact carrier 18, transmitter 20 and receiver 22 in this example are joined to the common assembly 16. This assembly 16 then as a whole is adhered to the flattened portion 30 in the hollow body 12. The contact carrier 18 in particular is formed in one piece, but might also be composed of several separate portions.

Figure 6:
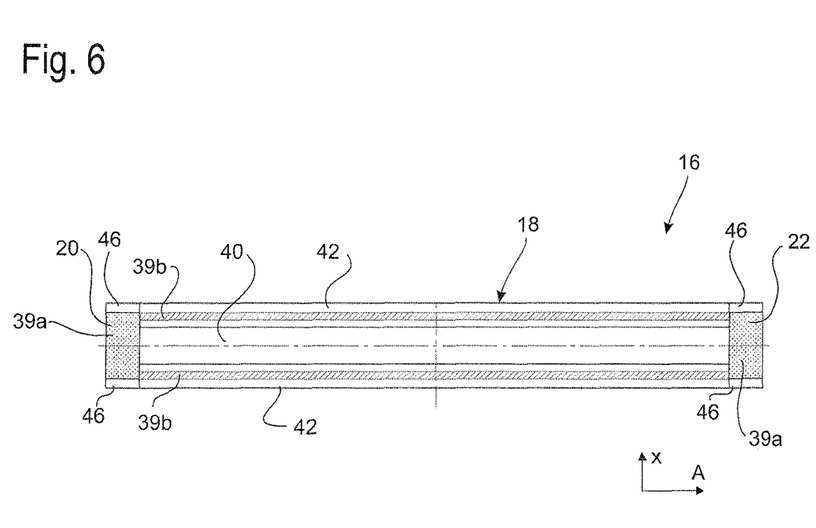
FIG. 6 shows a schematic representation of an assembly of a contact carrier, a transmitter and a receiver for a device according to the invention.

FIG. 6 shows the assembly 16 in the separate condition. It can clearly be seen that the longitudinal groove 40 is completely defined by the transmitter 20, the receiver 22 and the two longitudinal edges 42 of the contact carrier 18.

For attaching the transmitter 20 and the receiver 22 to the hollow body 12, an adhesive 39*a* with good acoustic conductivity is used here, whereas the longitudinal edges 42 are bonded to the hollow body 12 with an electrically conductive adhesive 39*b*. Suitable adhesives include known electrically or acoustically conductive adhesives.

From the short end faces of the contact carrier 18 two contact pins 46 each protrude in extension of the contact carrier 18, which serve for fastening the transmitter 20 and receiver 22, respectively.

On the printed circuit board forming the contact carrier 18, there are already formed the conductor paths which are required for the energy supply and signal transmission via the contact pins 46 to the transmitter 20 and to the receiver 22.

Transmitter 20 and receiver 22 are adhered to the contact pins 46 with the electrically conductive adhesive and positioned such that they terminate the longitudinal groove 40 on the end face.

In one variant, the control and evaluation unit 36 is accommodated in a housing of the device 10, as shown in FIG. 7. This can be an additional housing 48, but it can also be formed by a portion of the housing 26.

In another variant shown in FIG. 8, the control and evaluation unit 36 is arranged outside the housing 26 and an optional further housing 48 surrounding the same, wherein the cable 34 is guided out of the housing 26 and 48, respectively. Instead of a connection cable there might also exist a radio connection to the external control and evaluation unit 36.

The invention claimed is:

1. A device for determining properties of a medium, comprising a hollow body accommodating the medium, a housing circumferentially surrounding the hollow body, wherein at least one portion of a wall of the hollow body is formed as a waveguide for acoustic surface waves, the portion forming an interface to the medium, at least one transmitter for exciting acoustic waves in the waveguide, and at least one receiver for receiving acoustic waves from the waveguide, at least one transmitter and at least one receiver are arranged at a distance from each other, wherein the transmitter and the receiver are in direct contact with an outer surface of the waveguide, wherein the distance between transmitter and receiver is chosen such that acoustic waves excited by the transmitter can at least partly propagate on paths extending through the medium, and at least one contact carrier on which at least one of the transmitter and the receiver are arranged, and wherein a continuous air gap is formed between the waveguide and the contact carrier, and a filling mass completely fills the space between the hollow body, the contact carrier and the housing with the exemption of the air gap, wherein the contact carrier is different from the filling mass.

2. The device according to claim 1, wherein the filling mass consists of a material which absorbs acoustic waves excited by the transmitter.

3. The device according to claim 1, wherein several assemblies of contact carrier, transmitter and receiver are arranged distributed over the circumference of the hollow body.

4. The device according to claim 1, wherein radially inwards of the air gap a flattened portion is formed in the surface of the hollow body.

5. The device according to claim 1, wherein at least one of the transmitter and the receiver are bonded to the contact carrier.

6. The device according to claim 1, wherein at least one of the transmitter and the receiver are bonded to the contact carrier by at least one of an electrically and acoustically conductive adhesive.

7. The device according to claim 1, wherein the assembly of contact carrier, transmitter and/or receiver is prefabricated and as a whole attached to the hollow body.

8. The device according to claim 1, wherein the contact carrier is bonded to the waveguide.

9. The device according to claim 1, wherein the contact carrier is bonded to the waveguide by an electrically conductive adhesive.

10. The device according to claim 1, wherein a plug is attached to the contact carrier for contacting at least one of the transmitter and the receiver.

11. The device according to claim 1, wherein a plug is attached to the contact carrier by soldering for contacting at least one of the transmitter and the receiver.

12. The device according to claim 1, wherein the hollow body includes end-side fastening portions for the fluid connection with a fluid system.

13. A device for determining properties of a medium, comprising a hollow body accommodating the medium, a housing circumferentially surrounding the hollow body, wherein at least one portion of a wall of the hollow body is formed as a waveguide for acoustic surface waves, the portion forming an interface to the medium, at least one transmitter for exciting acoustic waves in the waveguide, and at least one receiver for receiving acoustic waves from the waveguide, at least one transmitter and at least one receiver are arranged at a distance from each other, wherein the transmitter and the receiver are in direct contact with an outer surface of the waveguide, wherein the distance between transmitter and receiver is chosen such that acoustic waves excited by the transmitter can at least partly propagate on paths extending through the medium, and at least one contact carrier on which at least one of the transmitter and the receiver are arranged, and wherein a continuous air gap is formed between the waveguide and the contact carrier, and a filling mass completely fills the space between the hollow body, the contact carrier and the housing with the exemption of the air gap, the contact carrier being formed by a printed circuit board.

14. A device for determining properties of a medium, comprising a hollow body accommodating the medium, a housing circumferentially surrounding the hollow body, wherein at least one portion of a wall of the hollow body is formed as a waveguide for acoustic surface waves, the portion forming an interface to the medium, at least one transmitter for exciting acoustic waves in the waveguide, and at least one receiver for receiving acoustic waves from the waveguide, at least one transmitter and at least one receiver are arranged at a distance from each other, wherein the transmitter and the receiver are in direct contact with an outer surface of the waveguide, wherein the distance between transmitter and receiver is chosen such that acoustic waves excited by the transmitter can at least partly propagate on paths extending through the medium, and at least one contact carrier on which at least one of the transmitter and the receiver are arranged, and wherein a continuous air gap is formed between the waveguide and the contact carrier, and a filling mass completely fills the space between the hollow body, the contact carrier and the housing with the exemption of the air gap, the contact carrier having a longitudinal groove which faces the hollow body and which defines the air gap together with the hollow body.

15. The device according to claim 14, wherein the longitudinal edges defining the longitudinal groove are adhered to the hollow body.

16. The device according to claim 15, wherein the longitudinal edges defining the longitudinal groove are adhered to the hollow body by an electrically conductive adhesive.

17. The device according to claim 14, wherein the transmitter and the receiver terminate the long-side ends of the longitudinal groove and the air gap.

* * * * *